(12) United States Patent
Hong et al.

(10) Patent No.: US 8,556,892 B2
(45) Date of Patent: *Oct. 15, 2013

(54) SYSTEMS AND METHODS FOR TRANSMURAL ABLATION

(75) Inventors: Jinback Hong, Maple Grove, MN (US); David E. Francischelli, Anoka, MN (US); Mark T. Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,477

(22) Filed: Aug. 14, 2012

(65) Prior Publication Data

US 2013/0072926 A1    Mar. 21, 2013

Related U.S. Application Data

(63) Continuation of application No. 13/117,690, filed on May 27, 2011, now Pat. No. 8,241,275, which is a continuation of application No. 11/780,911, filed on Jul. 20, 2007, now Pat. No. 7,959,626, which is a continuation of application No. 10/923,178, filed on Aug. 20, 2004, now Pat. No. 7,250,048, which is a continuation-in-part of application No. 10/364,553, filed on Feb. 11, 2003, now Pat. No. 6,989,010, which is a continuation-in-part of application No. 10/132,379, filed on Apr. 24, 2002, now Pat. No. 6,648,883.

(60) Provisional application No. 60/832,242, filed on Jul. 20, 2006, provisional application No. 60/923,365, filed on Apr. 13, 2007, provisional application No. 60/287,202, filed on Apr. 26, 2001.

(51) Int. Cl.
*A61B 18/18* (2006.01)

(52) U.S. Cl.
USPC .............................................. 606/34; 606/38

(58) Field of Classification Search
USPC .............................................. 606/34, 37–38
See application file for complete search history.

(56) References Cited

U.S. PATENT DOCUMENTS 6,080,149 A * 6/2000 Huang et al. ................... 606/32

* cited by examiner

*Primary Examiner* — Linda Dvorak
*Assistant Examiner* — Jaymi Della

(57) ABSTRACT

A method of applying ablation energy to achieve transmurality including applying ablation energy at a starting power to a tissue site and monitoring the impedance of the tissue site. A power applied to the tissue site can be reduced as a function of a rate of an increase in impedance according to some embodiments.

14 Claims, 13 Drawing Sheets

TIME TO FIRST POWER PLATEAU
(OVERALL n=208)

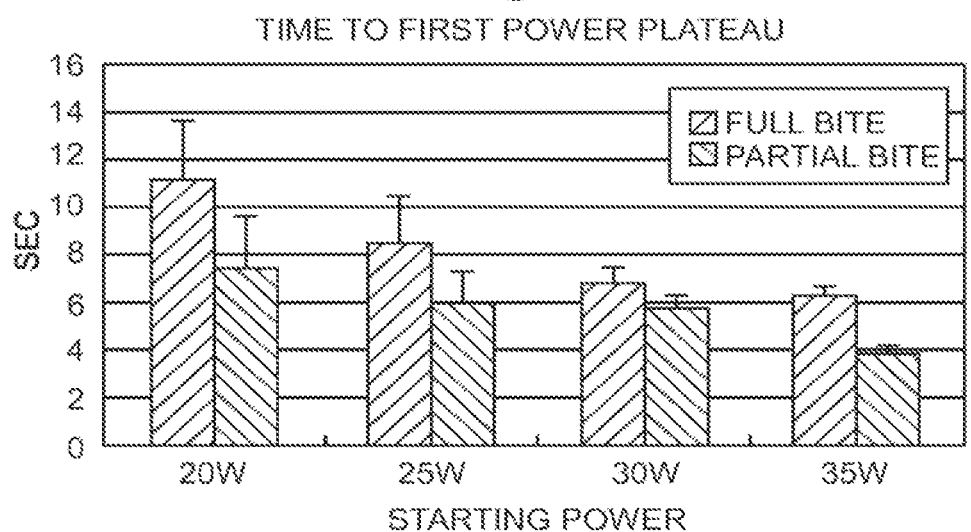
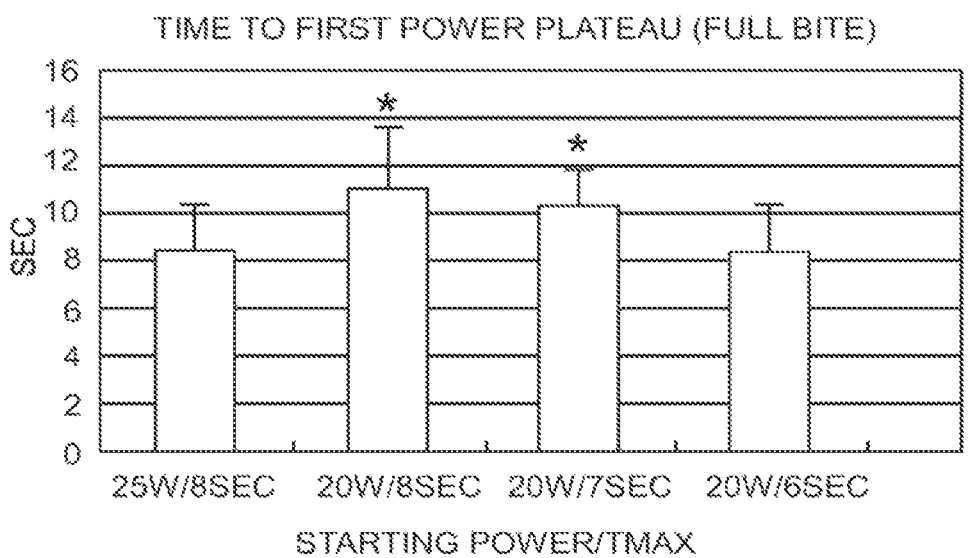

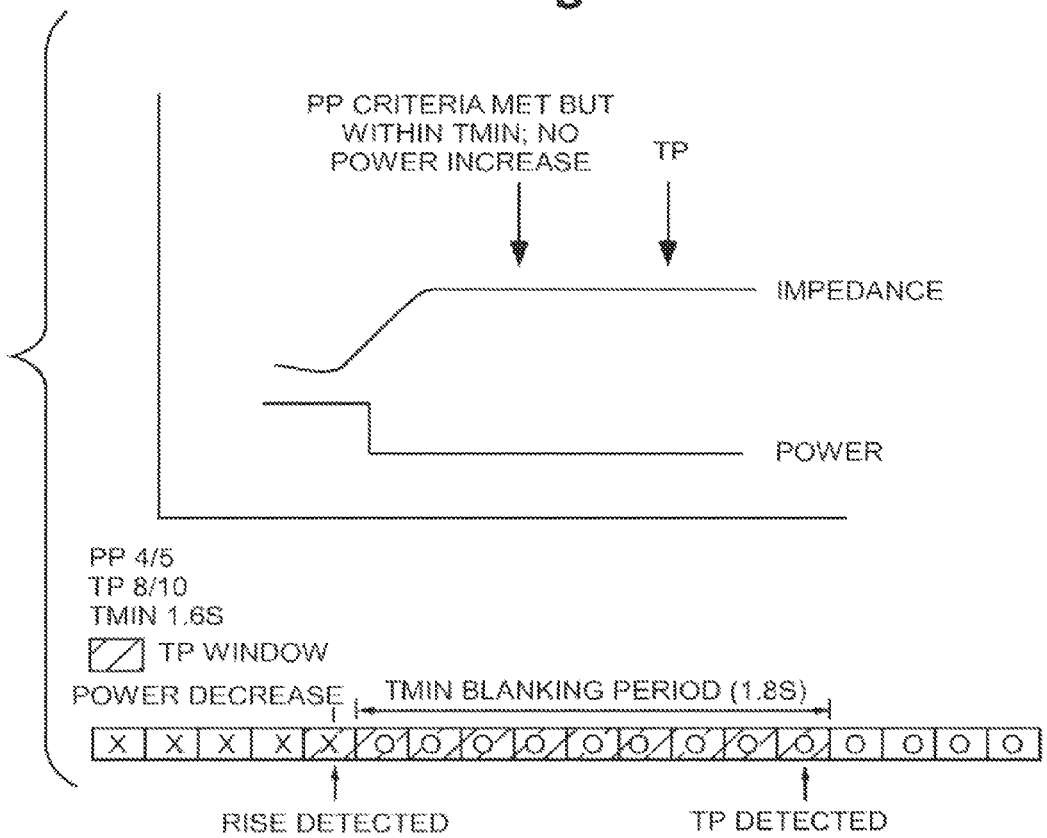

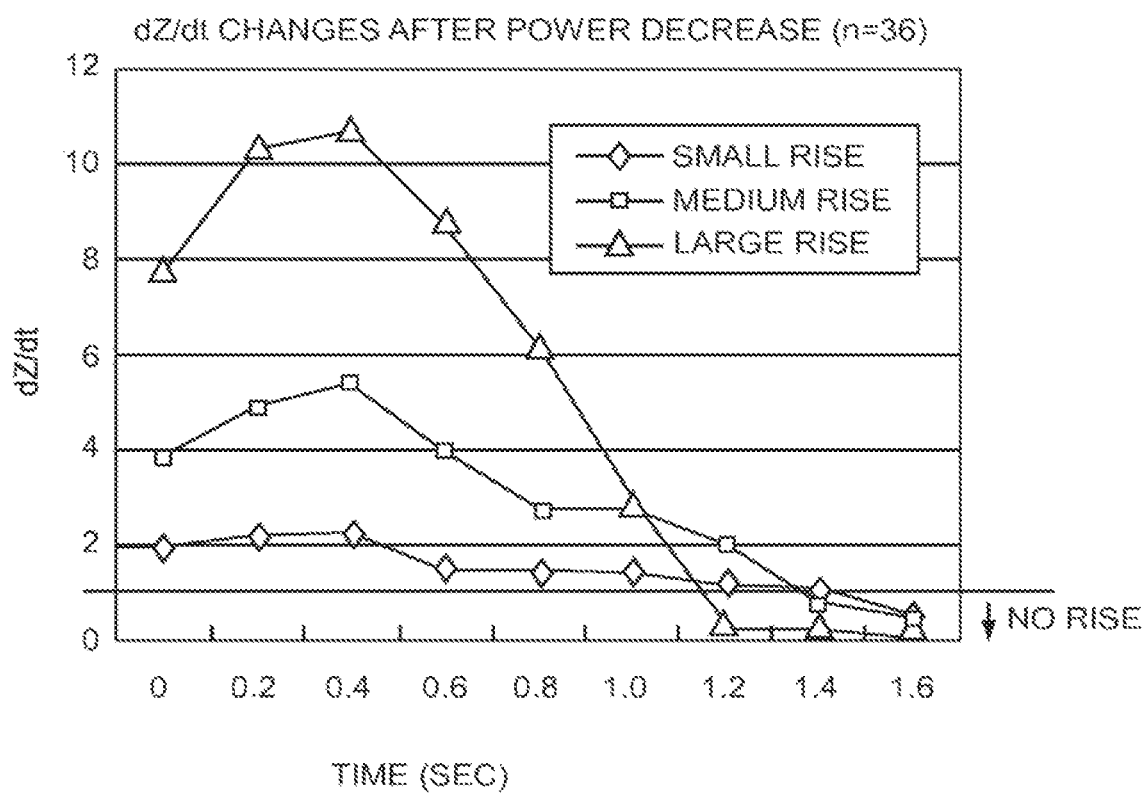

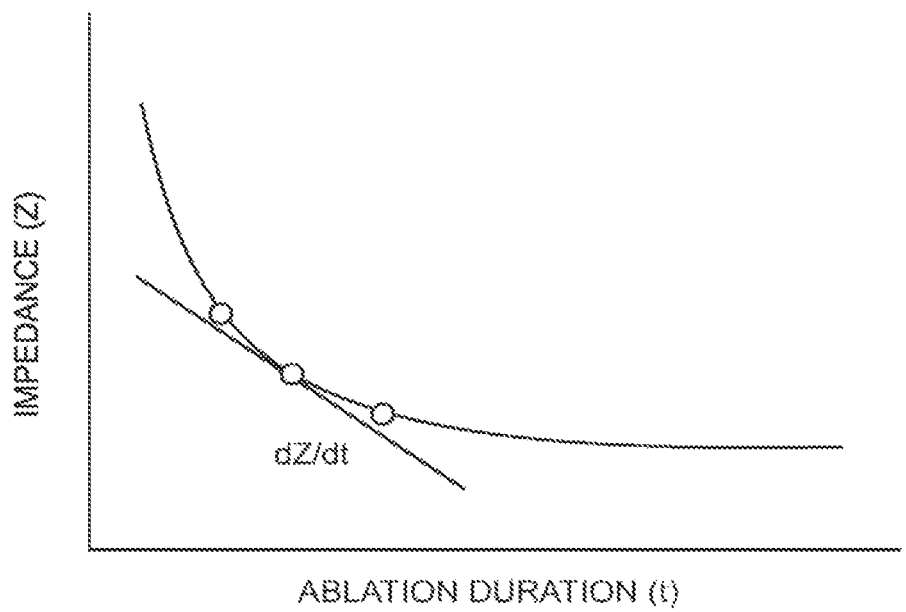

IMPEDANCE CONTROLLED (DECELERATED)

IMPEDANCE UNCONTROLLED (ACCELERATED)

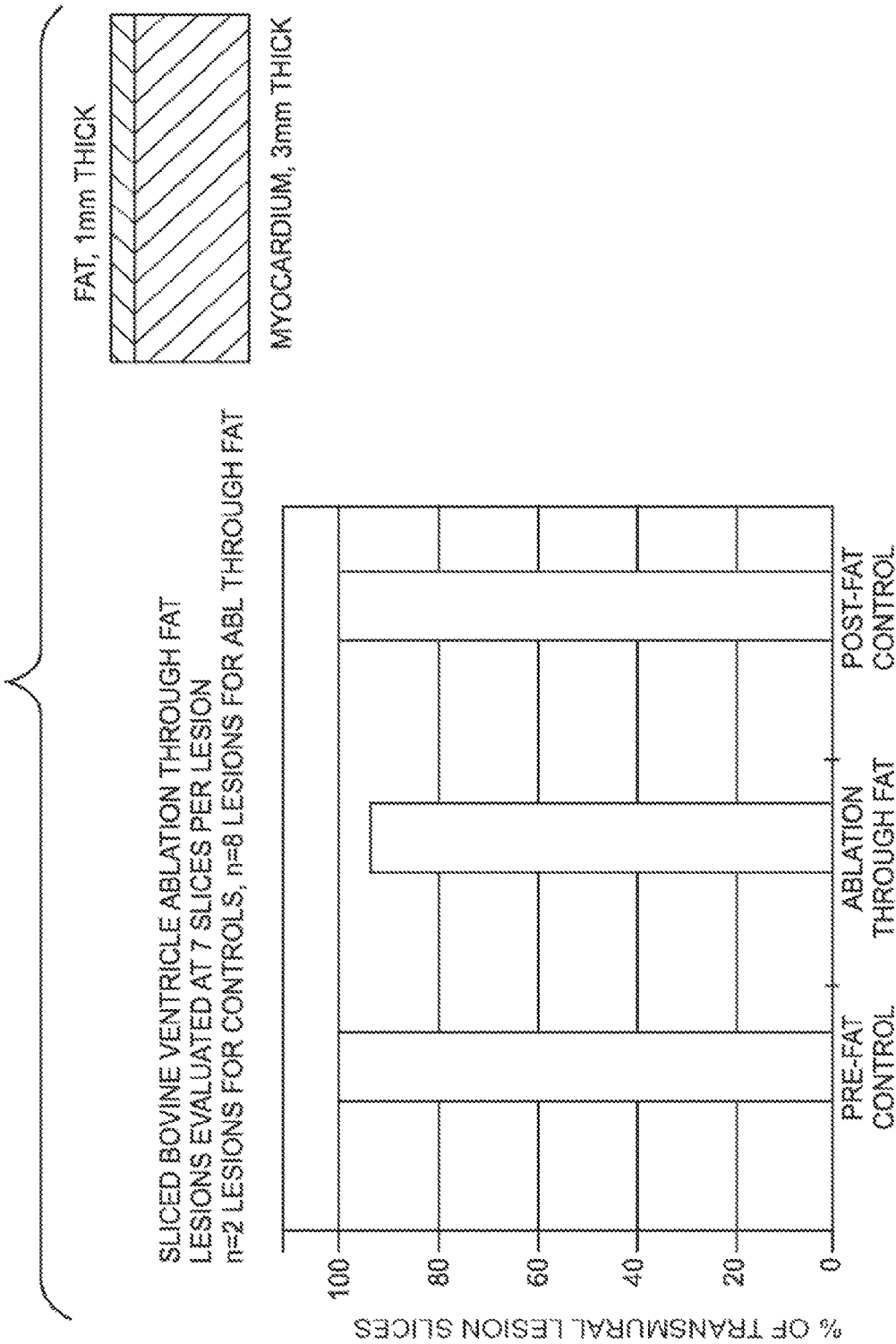

SYSTEMS AND METHODS FOR TRANSMURAL ABLATION

CROSS-REFERENCE TO RELATED APPLICATIONS

This application is a continuation of U.S. Ser. No. 13/117,690 filed May 27, 2011, now U.S. Pat. No. 8,241,275, issued on Aug. 14, 2012, which is a Continuation of U.S. Ser. No. 11/780,911, filed Jul. 20, 2007, now U.S. Pat. No. 7,959,626, issued on Jun. 14, 2011, that claims priority to U.S. Provisional Ser. No. 60/832,242 filed Jul. 20, 2006, and U.S. Provisional Ser. No. 60/923,365 filed Apr. 13, 2007, and which is a continuation-in-part of U.S. Ser. No. 10/923,178, filed Aug. 20, 2004, now U.S. Pat. No. 7,250,048, which is a continuation-in-part of U.S. Ser. No. 10/364,553, filed Feb. 11, 2003, now U.S. Pat. No. 6,989,010, which is a continuation-in-part application of U.S. Ser. No. 10/132,379, filed Apr. 24, 2002, now U.S. Pat. No. 6,648,883, which claims priority to U.S. Provisional Ser. No. 60/287,202, filed Apr. 26, 2001, the contents of each of which are hereby incorporated by reference in their respective entireties.

FIELD

Embodiments of the invention related generally to systems and methods for ablating tissue, and more particularly, to systems and methods for performing transmural ablations.

BACKGROUND

The Maze procedure is a surgical treatment for patients with chronic atrial fibrillation that is resistant to other treatments. The Maze procedure uses incisions in the right and left atria to divide the atria into electrically isolated portions, which in turn results in an orderly passage of the depolarization wave front from the sino-atrial node to the atrial-ventricular node, while preventing reentrant wave front propagation. Although successful in treating atrial fibrillation, the Maze procedure can be quite complex and is currently performed by a limited number of highly skilled cardiac surgeons in conjunction with other open-heart procedures. As a result of the complexities of the Maze procedure, there has been an increased level of interest in procedures employing electrosurgical devices or other types of ablation devices, (e.g., thermal ablation, micro-wave ablation, radio frequency or RF ablation, and cryo-ablation) to ablate tissue along pathways approximating the incisions of the Maze procedure.

Three basic approaches have been used to create elongated lesions with electrosurgical devices. The first approach is to create a series of short lesions using a contact electrode, moving it along the surface of the organ wall to be ablated to create a linear lesion. This can be accomplished either by making a series of lesions, moving the electrode between lesions, or by dragging the electrode along the surface of the organ to be ablated and continuously applying ablation energy. The second approach to creation of elongated lesions is to use an elongated electrode and to place the elongated electrode along the desired line of lesion along the tissue. The third approach to creation of elongated lesions is to provide a series of electrodes and arrange the series of electrodes along the desired line of lesion. The electrodes may be activated individually or in sequence. In the case of multi-electrode devices, individual feedback regulation of ablated energy applied via the electrodes may also be employed.

In conjunction with the use of electrosurgical ablation devices, various control mechanisms have been developed to control the delivery of ablation energy to achieve the desired result of ablation (i.e., killing of cells at the ablation site, while leaving the basic structure of the organ to be ablated intact). Such control systems include measurement of temperature and impedance at or adjacent to the ablation site, as disclosed in U.S. Pat. No. 5,540,681, issued to Struhl, et al.

Additionally, there has been substantial work done toward assuring that the ablation procedure is complete, i.e., that the ablation extends through the thickness of the tissue to be ablated, before terminating application of ablation energy. This desired result is sometimes referred to as a "transmural" ablation. For example, detection of a desired drop in electrical impedance of the tissue being ablated at the electrode site as an indicator of transmurality is disclosed in U.S. Pat. No. 5,562,721 issued to Marchlinski et al. Alternatively, detection of an impedance rise or an impedance rise following an impedance fall is disclosed in U.S. Pat. No. 5,558,671 issued to Yates and U.S. Pat. No. 5,540,684 issued to Hassler, respectively.

Previous transmurality algorithms were fundamentally based on the concept of identifying a flat impedance curve or plateau in response to an increase in power of ablation energy output to determine transmurality. However, there are many situations in which the flattened impedance curve does not remain plateaued long enough for the algorithm to determine that the flattened impedance curve indicates transmurality. The ablation is allowed to continue, which can sometimes cause the impedance curve to rise as a result of increased temperature (this usually occurs in fatty, inhomogeneous, or thicker tissues). Therefore, ablation is not terminated until the detection of an impedance rise followed by a minimum time delay or by reaching the high impedance limit. This is an inefficient method for performing a transmural ablation and can result in over-ablation.

SUMMARY

In one embodiment, the invention provides a method of applying ablation energy to achieve transmurality at a tissue site including applying ablation energy at a first power to the tissue site, monitoring impedance of the tissue site, and reducing the ablation energy applied to the tissue site to a second power as a function of a rate of increase of an identified rising impedance.

Other aspects of the invention will become apparent by consideration of the detailed description and accompanying drawings.

BRIEF DESCRIPTION OF THE DRAWINGS

FIG. 6 is a chart illustrating a comparison of time to first power plateau for various starting powers broken down by full bite measurements (tissue along full length of electrode) and partial bite measurements (tissue along partial length of electrode).

FIG. 7 is a chart illustrating a comparison of time to first power plateau for various maximum time values at a 20 W starting power.

FIG. 8 includes two charts illustrating a situation where transmurality plateau is detected without a power increase.

FIG. 9 is a chart illustrating a comparison of average dZ/dt value changes after a power decrease, with each rise (small, medium, and large rise) detected at t=0 seconds, and a dotted line indicating the boundary between no rise and small rise.

FIG. 12 is a chart illustrating a dZ/dt calculation.

FIG. 14 is a chart comparing lesion transmurality after ablating over fat for a previous algorithm versus an algorithm according to one embodiment of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
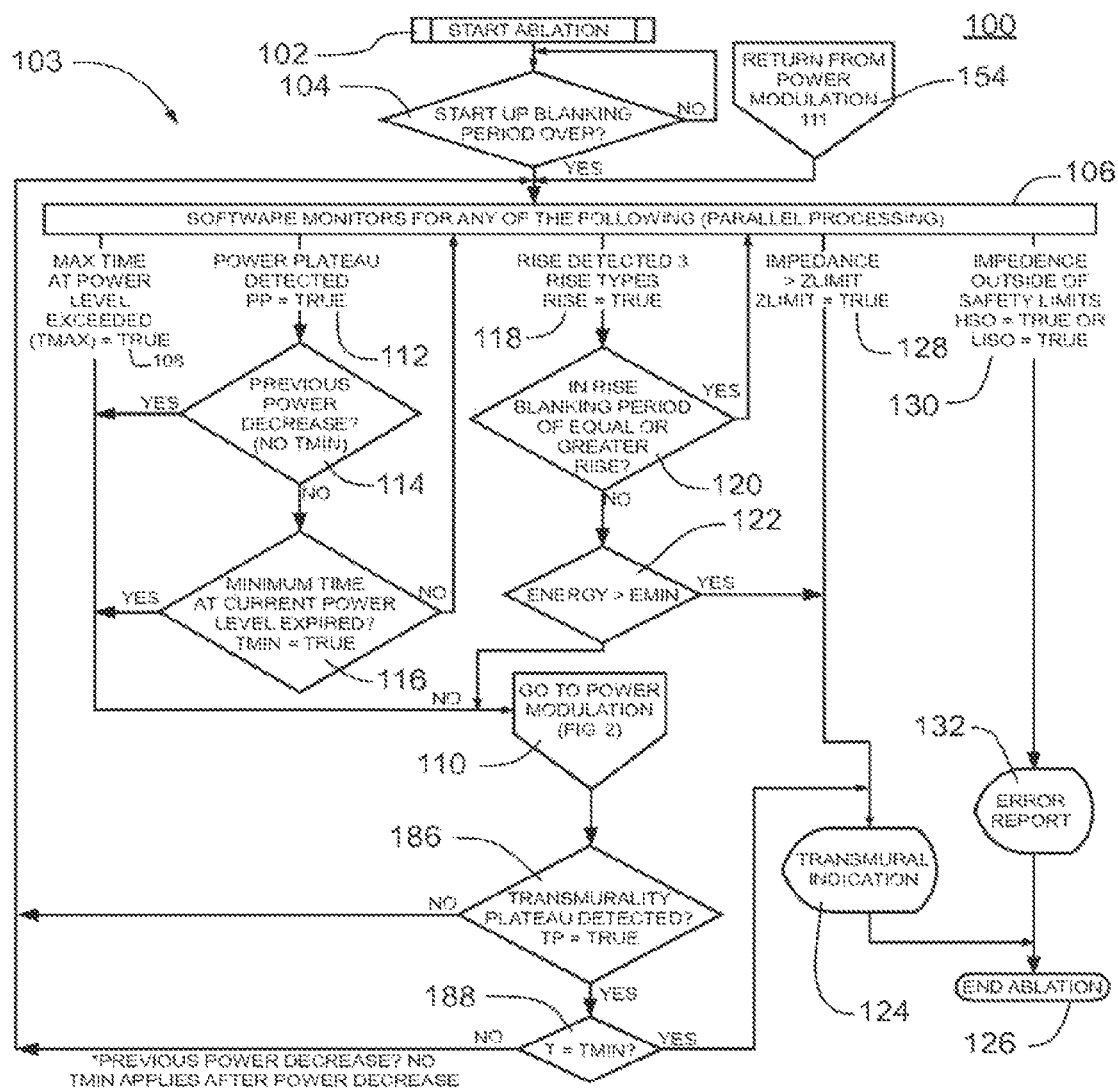
FIG. 1 is a flowchart depicting an algorithm for determining transmurality according to one embodiment of the invention.
Figure 2:
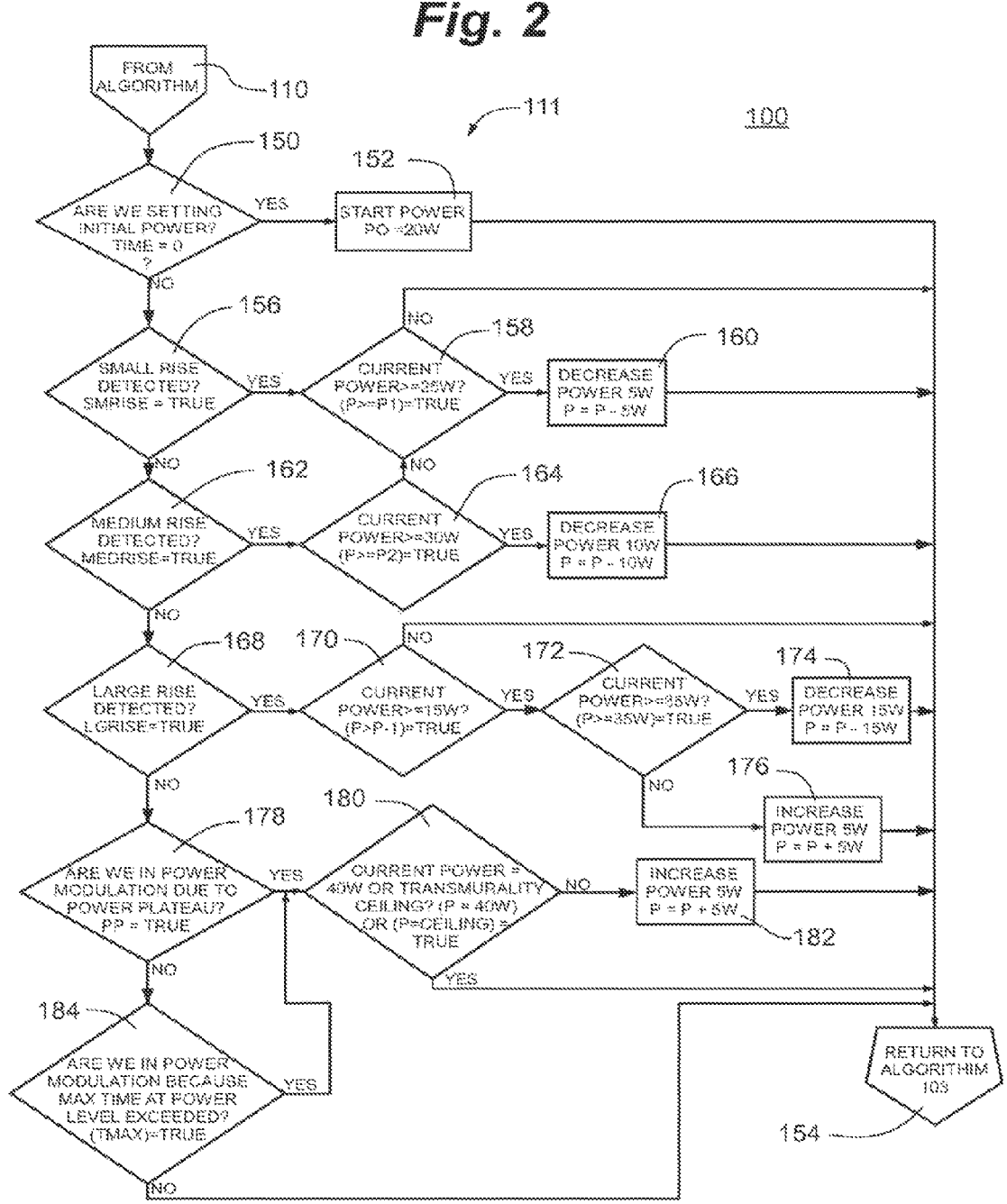
FIG. 2 is a flowchart depicting a power modulation algorithm according to one embodiment of the invention.

FIGS. 1 and 2 illustrate a method 100 of assessing transmurality of tissue being ablated and terminating delivery of ablation energy to an electrode in response to a plateau in impedance of the tissue in conjunction with a detected rise in impedance. The method 100 can be implemented during operation of an electrosurgical device to control the amount of ablation energy delivered by the device to the tissue and also to automatically terminate the delivery of ablation energy under certain conditions. The method 100 can be carried out by a controller having an electrical circuit or a software program, such as, for example, a microprocessor. The controller can be integrated into an electrosurgical device or electrically connected to the electrosurgical device. Data such as impedance measurements and temperature measurements that are used in the method 100 can be provided by sensors carried on the electrosurgical device. Likewise, the controller can be operably coupled to the output of the electrosurgical device to control the delivery of ablation energy to the electrode.

Figure 3:
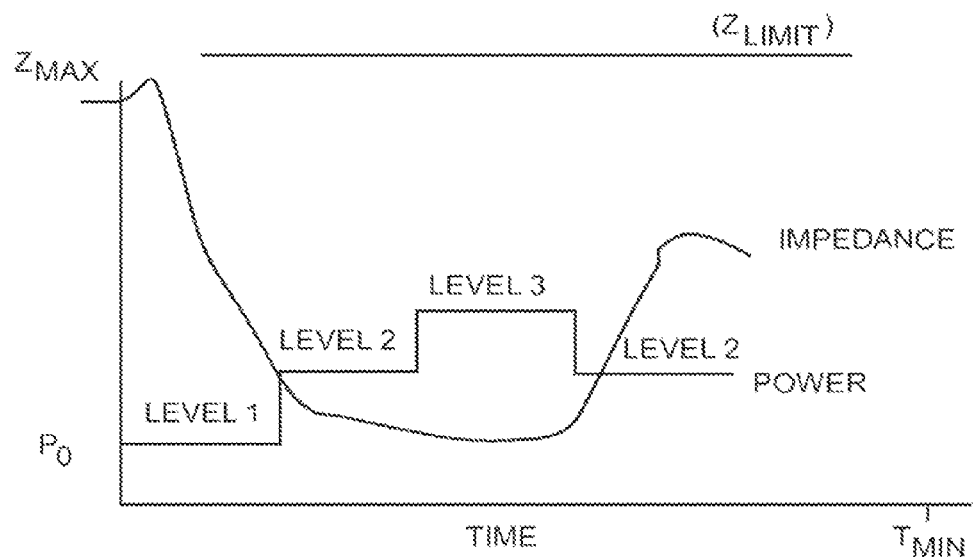
FIG. 3 is a chart illustrating an impedance versus power curve.

In general, the method 100 can monitor the tissue impedance profile or the impedance of the tissue being ablated as a function of time. During the early part of the ablation, the method 100 can gradually raise the power level of the ablation energy being delivered, while trying to detect a flattening of the tissue impedance profile. When a relatively flat impedance profile (or "power plateau") is discovered, the ablation power can be raised to a next level, as shown in FIG. 3. If there are no further changes in the tissue impedance profile (e.g., the impedance profile remains relatively flat after raising power in response to a power plateau), a transmurality plateau (TP) may be declared to exist. Transmurality, or the determination that the ablation procedure is complete (e.g., that the ablation extends through the thickness of the tissue to be ablated), may be indicated by any of several situations occurring, according to some embodiments of the invention. For example, if the total time of the ablation exceeds a minimum time delay ($T_{min}$) following a TP declaration, transmurality can be indicated. As another example, if the tissue impedance profile reaches an impedance limit ($Z_{limit}$) during ablation, transmurality can be indicated. As yet another example, if a rise in a certain parameter is detected (such as a rise in impedance or temperature), even if a TP has not been declared, and the rise occurs after a minimum total energy ($E_{min}$) has been delivered, transmurality can be indicated. Thus, embodiments of the invention provide a method of delivering an amount of energy to efficiently achieve a transmural ablation (e.g., reducing the time and/or energy expended to achieve a transmural ablation), while also minimizing the potential for over-ablation or tissue damage.

In order to prevent rapid impedance rises which can cause a high impedance shut off (HISO), for example, the method 100 can include a negative closed loop feedback system that can be kept active throughout the ablation. The negative closed loop feedback system can actively lower power output of the electrosurgical device if a rise in impedance is detected, according to some embodiments of the invention. The response of the closed loop feedback system may be based on how the rise in impedance is categorized, for example, according to one of three defined rise types. Thus, power can be actively modulated bi-directionally (e.g., positively or negatively) based on the slope of the impedance profile, for example, according to various embodiments of the invention.

Figure 4A:
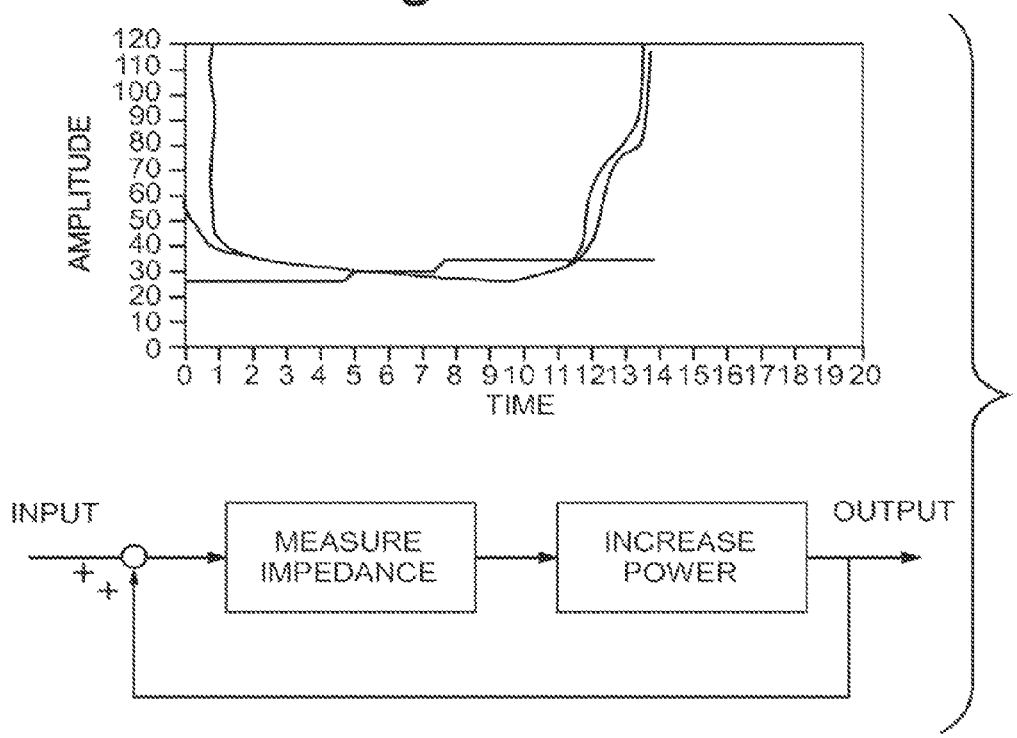
FIG. 4 includes two charts and two schematic diagrams illustrating an impedance profile and power output for positive closed loop feedback (a) and positive/negative closed loop feedback (b) systems.
Figure 4B:
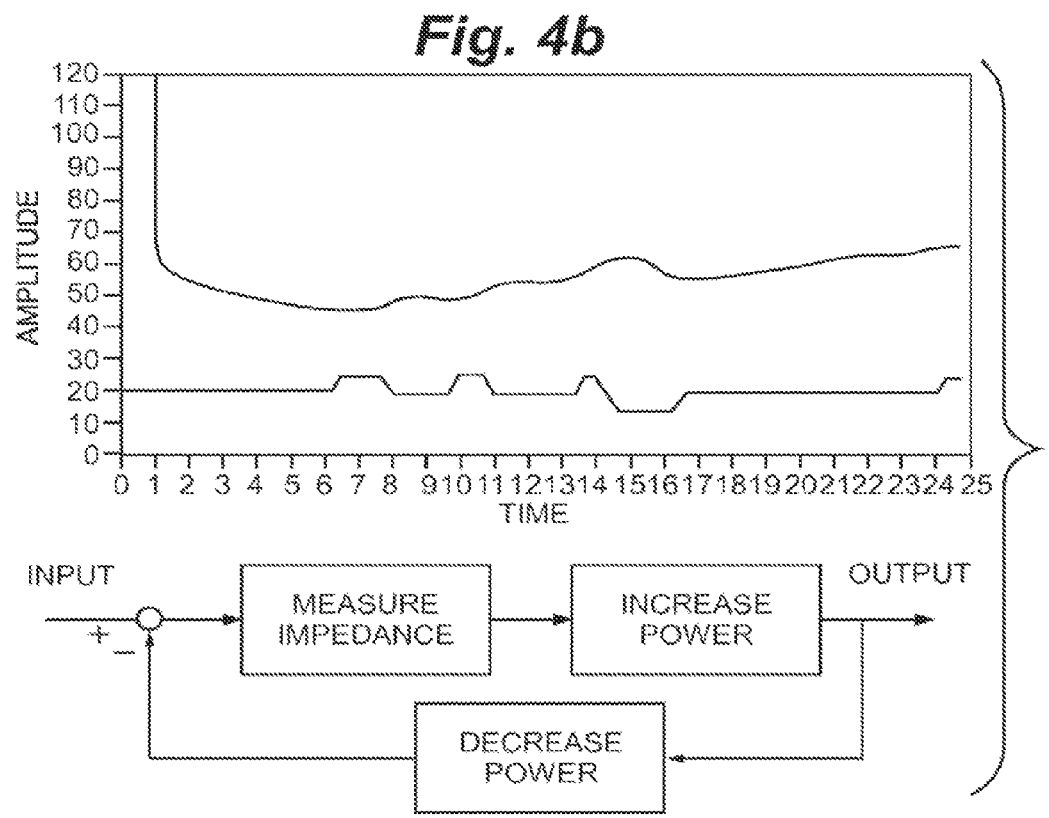

FIG. 4(a) illustrates an impedance profile and power level plot versus time of an algorithm for determining transmurality, in which power may only be increased (and not decreased) during the delivery of ablation energy. FIG. 4(b) illustrates a power level plot and resulting impedance profile of a method in accordance with some embodiments of the invention (such as method 100), in which power can be either increased or decreased as determined by the method.

Figure 5:
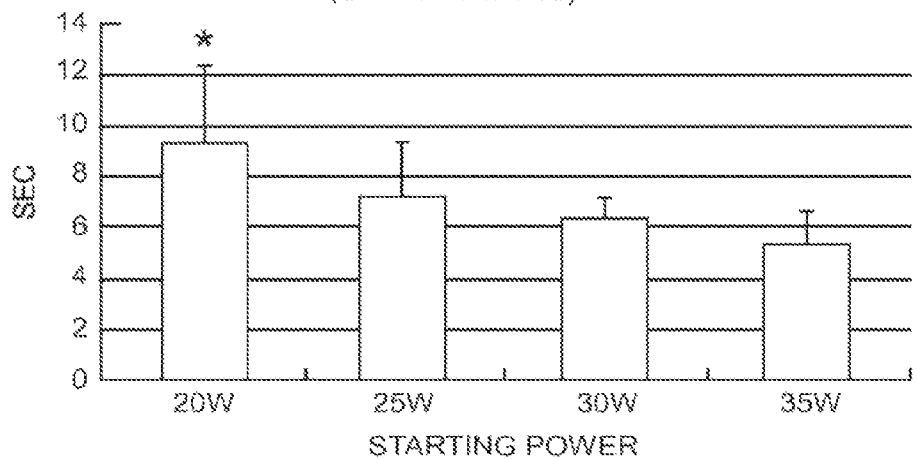
FIG. 5 is a chart illustrating a comparison of time to first power plateau for various starting powers.

As shown in FIG. 1, the ablation is initialized (at 102). A controller initiates delivery of ablation energy from an electrosurgical device to the tissue to be ablated and enters into a primary algorithm 103. The ablation energy may be delivered at a starting power, $P_0$. The starting power can contribute to an early impedance rise, which can occur within about ten seconds following the beginning of ablation. The starting power can also influence the rate of impedance decay until the impedance curve flattens, thus affecting overall ablation time. In some embodiments, the starting power, $P_0$, can be set to about 15 W, 20 W, 25 W, 30 W, or 35 W, as illustrated in FIGS. 5 and 6, or may be set to other values as deemed appropriate.

With continued reference to FIG. 1, the controller can determine (at 104) if a start-up blanking period has expired. The start-up blanking period, which can generally cover an initial ablation period, can be provided so that a sufficient number of measurements can be gathered before attempting to determine transmurality of an ablation lesion in tissue. The start-up blanking period can prevent erroneous data from previous ablations from being used in the analysis of the impedance profile and subsequent comparison to the criteria of plateaus (e.g., power plateaus and transmurality plateaus) and rise (e.g., impedance rise and temperature rise). The start-up blanking period can be set to start at t=0 during ablation (e.g., at the commencement of delivery of ablation energy to the tissue), and can have different lengths (e.g., it may be programmable and/or adjustable). In one possible embodiment, the start-up blanking period may be calculated using a formula that seeks to ensure sufficient data have been acquired prior to assessing transmurality. For example, the start-up blanking period may be defined as 1400+200*(y−1), wherein the start-up blanking period is a time period measured in milliseconds, and "y" is the number of dZ/dt calculations desired for making transmurality assessments. If the start-up blanking period has not yet expired, the controller can continue to deliver ablation energy at the starting power, for example. Once the start-up blanking period has expired, the controller can enter (at 106) a processing state in which a plurality of factors are processed or monitored in parallel with one another, while continuing to deliver ablation energy.

Various embodiments of the invention may allow the power level of the ablation energy to be varied (e.g., increased or decreased). In some embodiments, a maximum time may be specified for delivery of ablation energy at each of a number of different power levels. Thus, with reference to FIG. 1, a first factor can determine (at 108) whether a maximum time, $t_{max}$, at the current power level has been exceeded. The value for $t_{max}$ can be the same for each power level, or it can differ depending upon the power level. Tables 1(a)-(c) below illustrate examples of $t_{max}$ values for each of several exemplary power levels according to embodiments of the invention. It should be noted that the particular values in Tables 1(a)-(c) are purely illustrative in nature; one of ordinary skill would be able to modify these values to achieve similar results without departing from the scope of the invention as claimed. FIG. 7 illustrates the impact of $t_{max}$ on the amount of time it can take to reach a first "power plateau." If $t_{max}$ has not been exceeded, no action is taken relative to the first factor. The controller can continue to deliver ablation energy and can remain (at 106) in the parallel processing state. If $t_{max}$ has been exceeded, the controller can exit (at 110) the primary algorithm 103 and can enter a power modulation algorithm 111, as shown in FIG. 2. This can ensure that the ablation energy is applied at a given power level for no longer than the maximum time ($t_{max}$) associated with that power level before the controller goes to the power modulation algorithm 111.

TABLE 1(a)

Power Levels and Times

| Level | Power (W) | Power plateau blanking period ($t_{min}$), seconds | Max time ($t_{max}$), seconds |
|---|---|---|---|
| $P_{-1}$ | 15 | 1.80 | 2.00 |
| $P_0$ | 20 | 1.80 | 6.00 |
| $P_1$ | 25 | 1.80 | 6.00 |

TABLE 1(a)-continued

Power Levels and Times

| Level | Power (W) | Power plateau blanking period ($t_{min}$), seconds | Max time ($t_{max}$), seconds |
|---|---|---|---|
| $P_2$ | 30 | 1.80 | 6.00 |
| $P_3$ | 35 | 1.80 | 6.00 |
| $P_4$ | 40 | 1.80 | 35.00 |

TABLE 1(b)

Power Levels and Times

| Level | Power (W) | Power plateau blanking period ($t_{min}$), seconds | Max time ($t_{max}$), seconds |
|---|---|---|---|
| $P_{-1}$ | 20 | 2.00 | 4.0 |
| $P_0$ | 25 | 2.00 | 8.0 |
| $P_1$ | 30 | 2.00 | 8.0 |
| $P_2$ | 35 | 2.00 | 8.0 |
| $P_3$ | 40 | 2.00 | 8.0 |
| $P_4$ | 45 | 2.00 | 40.00 |

TABLE 1(c)

Power Levels and Times

| Level | Power (W) | Power plateau blanking period ($t_{min}$), seconds | Max time ($t_{max}$), seconds |
|---|---|---|---|
| $P_{-1}$ | 25 | 3.1 | 1.0 |
| $P_0$ | 30 | 3.1 | 5.00 |
| $P_1$ | 35 | 3.1 | 5.00 |
| $P_2$ | 40 | 3.1 | 5.00 |
| $P_3$ | 45 | 3.1 | 5.00 |
| $P_4$ | 50 | 3.1 | 30.00 |

As used above, a "power plateau," or flattened impedance profile, may occur during delivery of ablation energy to tissue. For example, the monitored impedance of the tissue being ablated is typically observed to decrease during delivery of ablation energy to tissue. At some point, the rate of decrease of the monitored impedance begins to level off (or flatten) during energy delivery. Such a power plateau may be indicated by a reduction in the absolute value of the slope of the monitored impedance during delivery of ablation energy, or by some comparable means of identifying a flattening of the impedance profile.

A second factor can determine (at 112) whether a power plateau, or a flattened impedance profile, has been detected. If no power plateau has been detected, no action is taken relative to the second factor. The controller can continue to deliver ablation energy and can remain (at 106) in the parallel processing state. If a power plateau has been detected, the controller can determine (at 114) whether there has been a previous power decrease. If there has been a previous power decrease, the controller can go (at 110) to the power modulation algorithm 111. If there has not been a previous power decrease, the controller can determine (at 116) whether a power plateau blanking period or minimum time per power ($T_{min}$) has expired. The power plateau blanking period prevents excessive power increases from occurring within a short period of time. It also allows time so that tissue responds to a power change before another power change is applied. Unlike previous algorithms which did not provide a decrease power, an algorithm according to the method 100 allows power to decrease. This power decrement may lead to a possibility of TP detection without power ever having increased (as shown in FIG. 8). In order to prevent this problem, the power plateau blanking period, $T_{min}$, may not apply after a power decrement, according to some embodiments. This can also reduce the possibility of detecting a TP at a power level less than the starting power (i.e., $P_{-1}$). During the power plateau blanking period, the power is not increased, in some embodiments. Data collected during the power plateau blanking period can be used for decision making following expiration of the power plateau blanking period. In some embodiments, the power plateau blanking period, or $T_{min}$, can be about 1.8 seconds for each power level, according to the example shown above in Table 1.

If the power plateau blanking period (i.e., the minimum time at the current power level) has expired, the controller can go (at 110) to the power modulation algorithm 111 (FIG. 2). If the power plateau blanking period has not expired, no action is taken relative to the second factor. Again, this means that the controller can continue to deliver ablation energy and can return (at 106) to the parallel processing state.

A third factor can determine (at 118) whether a rise has been detected. This can be an impedance rise or a temperature rise, for example. If no rise has been detected, no action is taken relative to the third factor. The controller can continue to deliver ablation energy and can remain (at 106) in the parallel processing state. If a rise has been detected, the controller can determine (at 120) whether a rise blanking period has expired. The rise blanking period can prevent excessive power increases due to the detection of multiple rises within a short period of time. The rise blanking period can also provide a minimum time so that impedance stabilizes after a power level change or modulation (as shown in FIG. 9). In some embodiments, the rise blanking period can be about 1.4 seconds. Data collected during the rise blanking period can be used for decision making following expiration of the rise blanking period.

If the rise blanking period has not yet expired, no action is taken relative to the third factor. The controller can continue to deliver ablation energy and can return (at 106) to the parallel processing state. If the rise blanking period has expired, the controller can determine (at 122) whether the total energy delivered by the electrosurgical device is greater than a minimum energy ($E_{min}$). Energy (Joules) is calculated as power (Watts)×time (seconds). For example, total energy can be calculated every 0.2 seconds as follows:

$$TotalEnergy(t = N \sec) = \sum_{n=1}^{5N} \frac{Power(n)}{5}$$

If the total energy delivered by the electrosurgical device is not greater than $E_{min}$, the controller can go (at 110) to the power modulation algorithm. If the total energy is greater than $E_{min}$, transmurality can be indicated (at 124) and the ablation (e.g., the delivery of ablation energy to a given tissue site) can be ended (at 126). $E_{min}$ can be selected to ensure that transmural lesions occur in every operating condition according to the algorithm of method 100. $E_{min}$ can be from about 300 J to about 500 J, in some embodiments.

A fourth factor can determine (at 128) whether the tissue impedance profile is greater than a maximum impedance ($Z_{limit}$). If the tissue impedance profile is less than or equal to $Z_{limit}$, no action is taken relative to the fourth factor. The controller can continue to deliver ablation energy and can remain (at 106) in the parallel processing state. If the tissue impedance profile is greater than $Z_{limit}$, transmurality can be indicated (at 124) and ablation can be ended (at 126).

A fifth factor can determine (at 130) whether the tissue impedance profile is greater than a high impedance shut off (HISO) limit. If the tissue impedance profile is not greater than the HISO limit, no action is taken relative to the fifth factor. This means that the controller can continue to deliver ablation energy and can remain (at 106) in the parallel processing state. If the tissue impedance profile is greater than the HISO limit, ablation can be ended (at 126) and an error report can be generated (at 132). The HISO limit can correspond to a safety limit of the tissue impedance profile. The fifth factor can limit the delivery of ablation energy regardless of the length of time ablation energy has been delivered, the power level of the ablation energy being delivered, or the indication of transmurality, etc.

As described above, a variety of conditions can cause the controller to exit the primary algorithm 103 and enter (at 110 in FIG. 1) the power modulation algorithm 111. FIG. 2 illustrates the power modulation algorithm 111. The power modulation algorithm 111 can be used to determine if and how to modulate the power level of the ablation energy, such as by increasing, decreasing, or maintaining the current power level.

Figure 10:
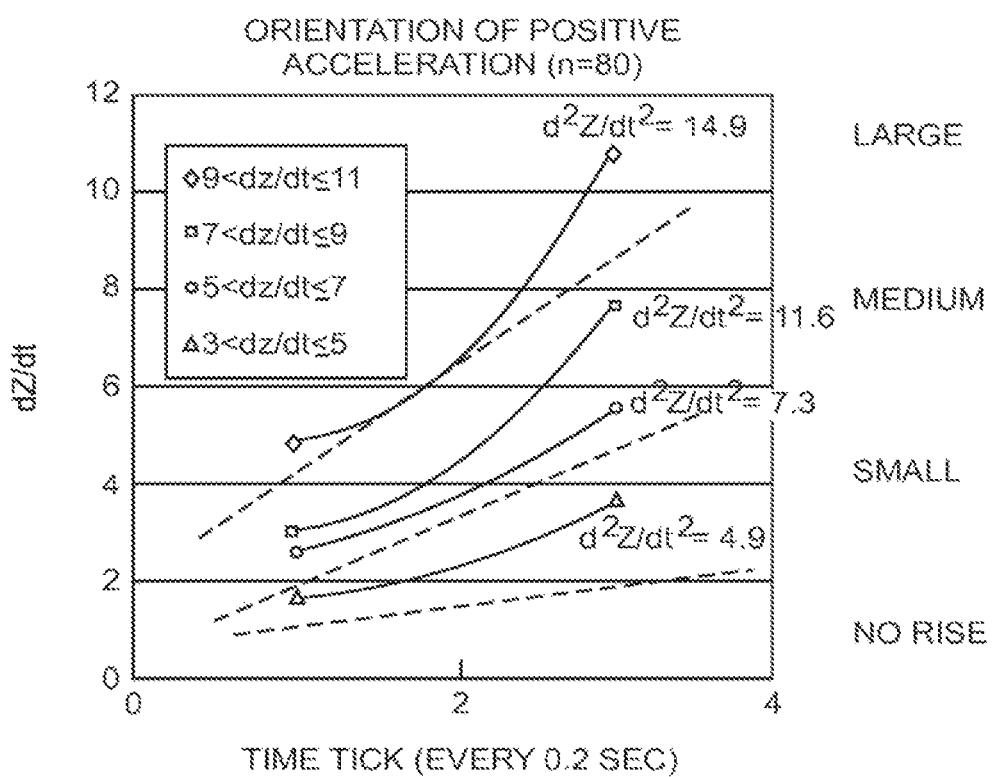
FIG. 10 is a chart illustrating a comparison of the direction of positive acceleration in different dZ/dt values, with dotted lines indicating boundaries between rise types.

As shown in FIG. 2, the controller can determine (at 150) if time is at zero, which corresponds to setting the starting power level. If time is not at zero, the starting power is set (at 152) and the controller can exit the power modulation algorithm 111 and return (at 154) to the primary algorithm 103. If the time is not zero, the controller can attempt to determine whether an impedance rise has been detected. A rise can be defined as a positive slope in the impedance profile, for example. In some embodiments, the impedance rise can be categorized according to the type of rise. For example, the magnitude of the slope may determine which type of impedance rise is occurring, including small, medium, and large impedance rises, as illustrated in FIG. 10. To determine the rise type, for example, a certain fraction of measured values (e.g., x out of y) must have a slope magnitude, dZ/dt, that exceeds a predetermined value, c. Tables 2(a) and 2(b) below provide exemplary values for x, y, and c for categorizing a rise in impedance as being a small, medium or large rise type. For example, using the criteria provided in Table 2(a), an impedance rise would be categorized as a "large" rise if 2 out of 4 measured values of impedance slope, dZ/dt, have a magnitude greater than 5.5.

$$\text{For } n = 1 \text{ to } y; \left|\frac{dZ}{dt}\right|_n > c$$

TABLE 2(a)

| | Plateau Variables | | | | |
|---|---|---|---|---|---|
| Variable | Power plateau | Transmurality plateau | Rise small | Rise medium | Rise large |
| x | 4 | 9 | 3 | 2 | 2 |
| y | 5 | 10 | 5 | 4 | 4 |
| c | 1.3 | 1.3 | 1.3 | 3 | 5.5 |

TABLE 2(b)

Plateau Variables

| Variable | Power plateau | Transmurality plateau | Rise small | Rise medium | Rise large |
|---|---|---|---|---|---|
| x | 6 | 13 | 4 | 3 | 3 |
| y | 7 | 14 | 7 | 6 | 6 |
| c | 1.5 | 1.5 | 1.5 | 3.1 | 6.8 |

In some embodiments, it may be desirable to further define a small rise as being, for example, 3 out of 5 measured values of impedance slope, dZ/dt, having a magnitude between 1.3 and 3 (e.g., the slope criteria for a medium rise). Similarly, it may be desirable in some embodiments to define a medium rise as being, for example, 2 out of 4 measured values of impedance slope, dZ/dt, having a magnitude between 3 and 5.5 (e.g., the slope criteria for a large rise).

If a small rise is detected (at 156), the controller can determine (at 158) if the current power is greater than a preset maximum corresponding to the small rise. In some embodiments, the preset small rise maximum power can be 25 W, for example. If the current power level is greater than or equal to the preset small rise maximum, power can be decreased (at 160) by a specified amount, for example, by 5 W. At that point, the controller may exit (at 154) the power modulation algorithm 111 and return to the primary algorithm 103. If the current power is less than the preset small rise maximum, the controller can exit (at 154) the power modulation algorithm 111 and can return to the primary algorithm 103 without modulating the power.

If a small rise is not detected (at 156), but a medium rise is detected (at 162), the controller can determine (at 164) if the current power is greater than a preset maximum corresponding to the medium rise. In one embodiment, the preset medium rise maximum power level is 30 W. If the current power is greater than or equal to the preset medium rise maximum, power can be decreased (at 166) by a certain amount, for example 10 W, and the controller can return (at 154) to the primary algorithm 103. If the current power is less than the preset medium rise maximum, the controller can return to the small rise determination (at 158) and can continue from there.

If a medium rise is not detected (at 162), but a large rise is detected (at 168), the controller can determine (at 170) if the current power level is greater than a preset minimum corresponding to the large rise. In one embodiment, the preset large rise minimum can be 15 W. If the current power is less than the preset large rise minimum, the controller can return (at 154) to the primary algorithm 103 without modulating the power. If the current power is greater than or equal to the preset large rise minimum, the controller can determine (at 172) if the current power is greater than or equal to a preset large rise maximum. If the current power is greater than or equal to the preset large rise maximum (e.g., 35 W), power can be decreased (at 174) by a certain amount, for example 15 W, and the controller can return (at 154) to the primary algorithm 103. If the current power is less than the preset large rise maximum, the controller can increase power (at 176) by a certain amount, for example 5 W, and can return (at 154) to the primary algorithm 103. In one embodiment, the preset large rise maximum can be 35 W.

Figure 11:
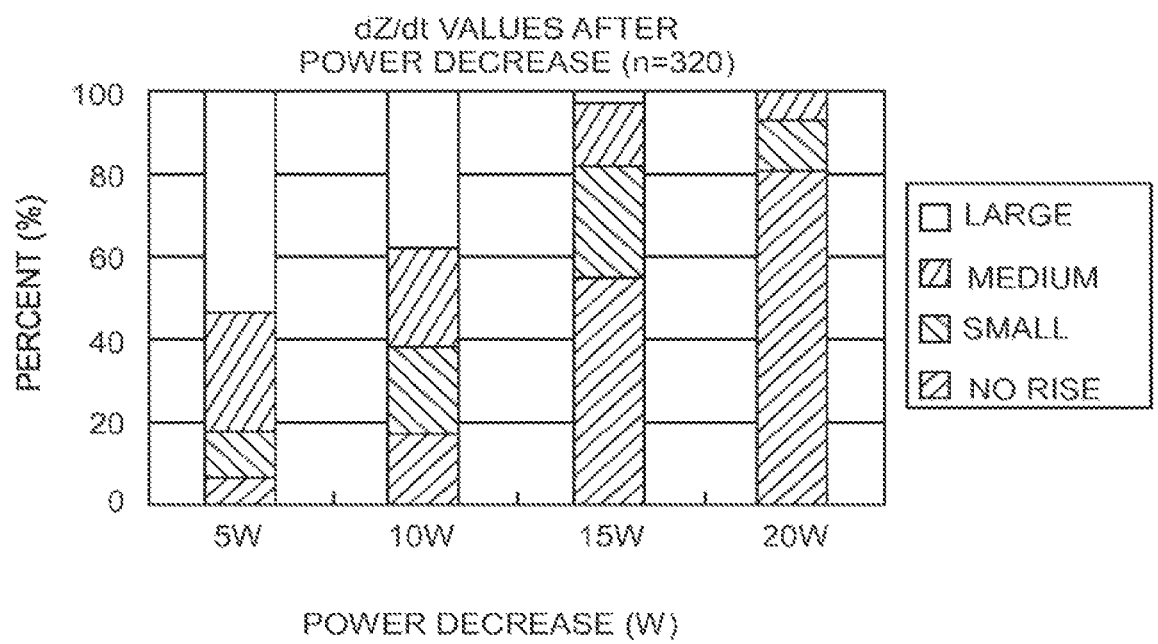
FIG. 11 is a chart illustrating a frequency plot of dZ/dt values at 1.4 seconds after a power decrement.

FIG. 11 illustrates a frequency plot of impedance slope (dZ/dt) values at 1.4 seconds after a power decrement. In FIG. 11, the dZ/dt values were categorized according to rise type (no rise, small, medium, and large rise), and the frequency of occurrence of each rise type is shown for each of the following power decrement amounts: 5 W, 10 W, 15 W, and 20 W. Table 3 below shows the decrement and minimum power level for each of the three rise types.

TABLE 3

Power decrement values and minimum power

| | Rise types | | |
|---|---|---|---|
| | Small | Medium | Large |
| Decrease amount | 5 watts | 10 watts | 15 watts |
| Minimum power level | $P_0$ | $P_0$ | $P_{-1}$ |

If none of a small, medium, or large rise is detected, the controller can determine (at 178) whether the power modulation algorithm 111 was entered due to a power plateau. If so, the controller can determine (at 180) if the current power is at a maximum power or the transmurality ceiling. In some embodiments, the maximum power can be a predetermined value, for example 40 W. If the current power level is either at the maximum power or at the transmurality ceiling, the controller can exit the power modulation algorithm 111 and can return (at 154) to the primary algorithm 103 without modulating the power. If the current power is not equal to either the maximum power or the transmurality ceiling, power can be increased (at 182) by a certain amount, for example 5 W, in some embodiments. The controller can then return (at 154) to the primary algorithm 103.

If none of a small, medium, or large rise has been detected and the power modulation algorithm 111 was not entered due to a power plateau, the controller can determine (at 184) if the power modulation algorithm 111 was entered because the maximum time ($t_{max}$) at a power level had been exceeded. If so, the controller can determine (at 180) if the current power is at a maximum power or the transmurality ceiling, substantially as described above. If not, the controller can return (at 154) to the primary algorithm 103.

Returning to FIG. 1, upon return (at 154) from the power modulation algorithm 111 to the primary algorithm 103, the controller returns (at 106) to the parallel processing state. In addition, concurrently with the controller entering the power modulation algorithm 111, the controller may also continue (at 186) with the primary algorithm 103.

The controller can determine (at 186) whether a transmurality plateau has been detected. If no transmurality plateau has been detected, the controller can return (at 106) to the parallel processing state. If a transmurality plateau has been detected, the controller may next determine (at 188) whether a minimum time per ablation ($T_{min}$) has expired. If $T_{min}$ has not expired, no further action is taken, the controller can continue to deliver ablation energy and can return (at 106) to the parallel processing state. If $T_{min}$ has expired, transmurality can be indicated (at 124) and ablation can be ended (at 126). The minimum time per ablation, $T_{min}$, can be about 10-30 seconds in some embodiments, as shown below in the exemplary groups of settings (Settings A-C) of Table 4, which also provides examples of other variable settings.

TABLE 4

Transmurality Mode Settings

| Variable | Description | Setting A | Setting B | Setting C |
|---|---|---|---|---|
| $t_1$ | Start time to check for $Z_{max}$ | 0.2 sec. | 0.3 sec. | 0.1 sec. |

TABLE 4-continued

Transmurality Mode Settings

| Variable | Description | Setting A | Setting B | Setting C |
|---|---|---|---|---|
| $t_2$ | Stop time to check for $Z_{max}$ | 2.0 sec. | 1.5 sec. | 2.2 sec. |
| $T_{max}$ | Maximum time per ablation | 40 sec. | 45 sec. | 50 sec. |
| $T_{min}$ | Minimum time per ablation | 19 sec. | 22 sec. | 24 sec. |
| $P_{max}$ | Maximum Power (watts) | 40 watts | 45 watts | 50 watts |
| Scale | Offset scale multiplier for $Z_{min}$ | 2.8 | 3.0 | 2.5 |
| | Transmurality Shutoff: | Manual Shutoff | Manual Shutoff | Manual Shutoff |

In some embodiments, detection of a transmurality plateau can require that dZ/dt be greater than or equal to 1.3 for 9 out of 10 points in a detection window, as indicated in Table 2 (above). Requiring a significant number of the points in the detection window to satisfy the transmurality plateau criteria may ensure that there is only one power increment arising from the power modulation algorithm 111 in a transmurality plateau detection window.

To reduce the possibility of severe over-ablation, a maximum total ablation time ($T_{max}$) for creating an ablation lesion or for performing an ablation procedure can be imposed. In one embodiment, the maximum total ablation time is about 40 seconds, as indicated in the example shown in Table 4. When $t_{max}$ is reached, power delivery can be terminated regardless of the transmurality determination. In one embodiment, the controller may indicate an error condition to the user when power delivery is terminated due to maximum total ablation time, $t_{max}$, being reached. This indication can be an audible indicator, a visual indicator, or a combination of both.

In some embodiments, the tissue impedance (Z) can be measured or calculated about every 0.2 seconds, for example. However, in some circumstances, there can be a significant amount of noise in the signal. To reduce the effects of this noise, the data can be filtered. One example of a filtering method to reduce the effects of noise can be accomplished using a 5-point moving average of the measured impedance values:

$$Z = \left[\frac{Z_{t-2} + Z_{t-1} + Z_t + Z_{t+1} + Z_{t+2}}{5}\right]$$

The 5-point moving average may result in the filtered impedance lagging the measured impedance values by about 400 msec in embodiments in which impedance is measured or calculated every 200 msec, for example.

The tissue impedance profile, or the rate of change in impedance per unit time (dZ/dt), can be calculated from the measured impedance values (e.g., without filtering), or from filtered impedance data (e.g., using the 5-point moving average), with a 3-point central difference algorithm, as shown in FIG. 12, and as described by the following equation:

$$\frac{dZ}{dt} = \frac{1}{2\Delta t}(Z_{t+1} - Z_{t-1})$$

The rate of change in impedance per unit time, dZ/dt, can therefore lag the filtered impedance by about 200 msec in some embodiments. To identify regions of the tissue impedance profile as a "rise" or a "plateau," a rolling window of dZ/dt points can be examined.

The method of assessing transmurality and terminating delivery of ablation energy to an electrode as described in relation to FIGS. 1 and 2 is based on the concept of finding a flat impedance profile or plateau. When the algorithm finds a flat impedance curve, it may raise power to a next level. If there are no further changes in the impedance profile, a transmurality plateau can be declared.

A plateau can be defined as a flattening of the impedance curve. To determine a plateau, the absolute value of a certain number (e.g., x out of y) of the dZ/dt points must be less than or equal to some defined slope value, c, wherein y is the number of points in the detection window:

For $n = 1$ to $y$;

$$\left|\frac{dZ}{dt}\right|_n \leq c$$

There are two types of plateaus—power plateaus and a transmurality plateaus—that may be defined, for example, by using different values for x and y, and having different responses (e.g., x out of y impedance slope values meeting certain criteria). Table 2 above shows examples of different criteria for identifying power and transmurality plateaus. When a power plateau is reached, the controller can increment the power level of the ablation energy to a next (e.g., higher) level. In some embodiments, a power plateau blanking period may also be established and used, whereby the criteria for identifying a power plateau is not evaluated until the completion of the power plateau blanking period. Such a power plateau blanking period may be employed, for example, following a change in power level of the ablation energy. When a transmurality plateau is reached, a transmurality flag can be set, and, in some embodiments, power cannot be increased beyond the power level at which the transmurality plateau was detected (e.g., the power level at which a transmurality plateau is identified may define a "ceiling" on the power level, or a "transmurality ceiling," according to some embodiments). Power can be allowed to be decreased and increased according to the power modulation criteria after a transmurality plateau is identified, but the ceiling cannot be exceeded, in some embodiments, as indicated at 180 in FIG. 2. When a transmurality plateau is detected at the same time that a power plateau is detected, the transmurality plateau rule may supersede the power plateau rule and power may remain at the same level, according to some embodiments of the invention.

The rise blanking period may be applied in certain situations. For example, in some embodiments, the rise blanking period is applied only in situations where a given rise (e.g., impedance rise or temperature rise) is of the same level (e.g., small, medium, or large) or below the level of a preceding rise. For example, the rise blanking period may apply between successive rises of equal type, or may apply when a medium rise occurs following a large rise, or when a small rise follows either a medium or a large rise.

Figure 13A:
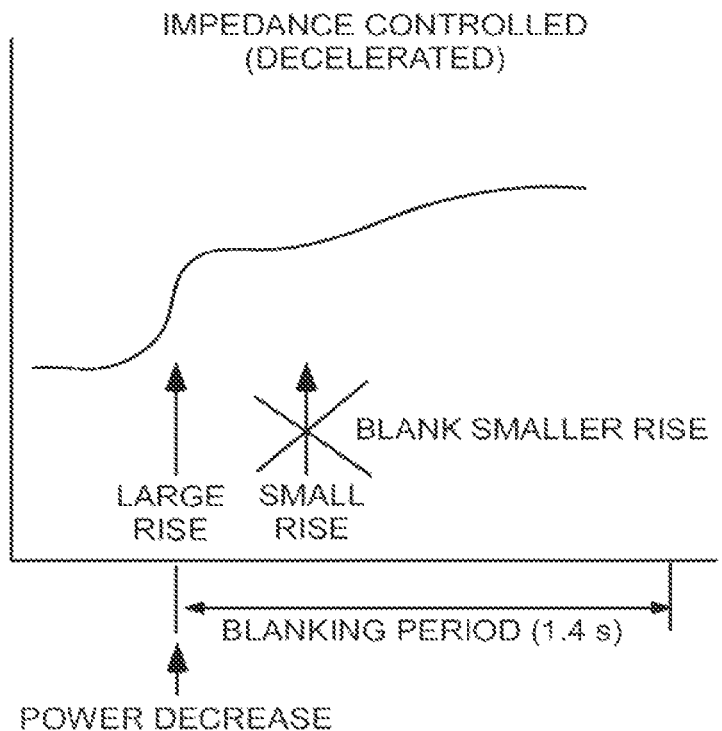
FIG. 13 is a chart illustrating an impedance profile in which a larger rise followed by a smaller rise is blanked (a), while a smaller rise followed by a larger rise is not blanked (b).
Figure 13B:
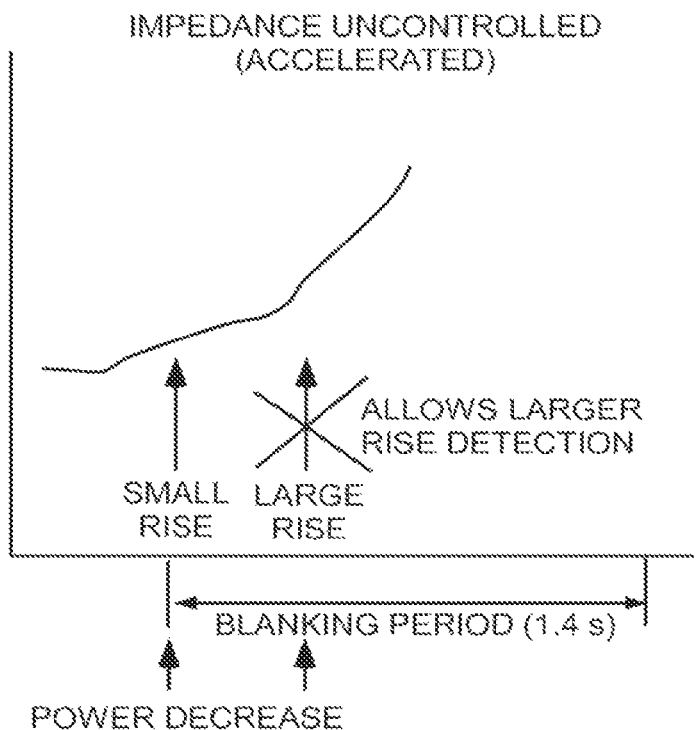

To further illustrate by way of example, if a medium rise is detected while ablating at 35 W, a 10 W reduction in power may be implemented according to the power modulation algorithm illustrated in FIG. 2. For the duration of the rise blanking period, or the next 1.4 seconds, while ablating at the reduced level of 25 W, the algorithm can be blanked from acting again on small or medium rises. This can allow time for the tissue impedance to stabilize and can reduce the rate of rise without overreacting and lowering power levels excessively. However, if a large impedance rise should be detected during the rise blanking period, the algorithm can immediately reduce power by 15 W or to a minimum power of 15 W, for example, regardless of the blanking period (e.g., the blanking period is ignored). FIG. 13 illustrates the application of the rise blanking period. In FIG. 13(*a*), a larger rise followed by a smaller rise is blanked, while in FIG. 13(*b*), a smaller rise followed by a larger rise is not blanked. If impedance is still rising after the rise blanking period expires, another power reduction can be implemented according to the algorithm of method 100.

Table 5 below provides a number of groups of exemplary settings and criteria (Settings A-C) that may be employed by a transmurality control algorithm according to some embodiments of the invention.

In the method 100 of FIGS. 1 and 2, the occurrence of rapid impedance rises that might lead to a $Z_{limit}$ or to HISO condition have been reduced so that an ablation that fails to result in a TP will continue, running past $T_{min}$ and potentially all the way to $t_{max}$. However, the determination of the total amount of energy is used to provide an indication of transmurality in situations when a TP is not detected, thereby reducing instances in which ablation energy continues to be delivered until $t_{max}$. Energy provides a linear criteria in a relation of the formation of ablation lesions. The value for $E_{min}$ can be based on the maximum energy value which produces non-transmural lesions, along with an additional margin.

As shown below in Table 6, energy values from 340 J to 500 J with 20 J intervals at a fixed 20 W starting power can result in varying transmurality outcomes. In one example, reliable transmural lesions occurred with any value above 400 J using 20 W fixed power. The value 400 J is not necessarily, however, a minimum energy, since power can be reduced to $P_{-1}$, or the

TABLE 5

Exemplary criteria and settings for the algorithm of FIGS. 1 and 2

|  | Setting A | Setting B | Setting C |
|---|---|---|---|
| Starting Power, $P_0$ | 20 W | 25 W | 30 W |
| Available Powers | 15, 20, 25, 30, 35, and 40 W | 20, 25, 30, 35, 40, and 45 W | 25, 30, 35, 40, 45, and 50 W |
| Power plateau criteria | 4/5 pts $\|dZ/dt\| = 1.3$ | 6/7 pts $\|dZ/dt\| = 1.5$ | 6/7 pts $\|dZ/dt\| = 1.5$ |
| $t_{max}$ (maximum time per power) | 6 sec 2 sec for $P_{-1} = 15$ W | 8 sec 4 sec for $P_{-1} = 20$ W | 5 sec 1 sec for $P_{-1} = 25$ W |
| $t_{min}$ (power plateau blanking period) | 1.8 sec | 2.0 | 3.1 |
| $T_{min}$ (minimum time per ablation) | 19 sec | 22 sec | 24 sec |
| Transmurality plateau | 9/10 pts $\|dZ/dt\| = 1.3$ | 13/14 pts $\|dZ/dt\| = 1.5$ | 13/14 pts $\|dZ/dt\| = 1.5$ |
| Rise criteria | three rise types: 3/5 pts dZ/dt > 1.3 (small), 2/4 pts dZ/dt > 3 (med), or 2/4 pts dZ/dt > 5.5 (large)) | three rise types: 4/7 pts dZ/dt > 1.5 (small), 3/6 pts dZ/dt > 3.1 pts (med), or 3/6 pts dZ/dt > 6.8 (large)) | three rise types: 4/7 pts dZ/dt > 1.5 (small), 3/6 pts dZ/dt > 3.1 pts (med), or 3/6 pts dZ/dt > 6.8 (large)) |
| Step down after rise detection | Small: by 5 W (no less than 20 W) Medium: by 10 W (no less than 20 W) Large: by 15 W (no less than 15 W) | Small: by 5 W (no less than 20 W) Medium: by 10 W (no less than 20 W) Large: by 15 W (no less than 15 W) | Small: by 5 W (no less than 20 W) Medium: by 10 W (no less than 20 W) Large: by 15 W (no less than 15 W) |
| After Rise detection | 1.4 sec blanking between rises of the same size; 1.4 sec blanking at med rise after large rise; 1.4 sec blanking at small rise after either med or large rise | 1.4 sec blanking between rises of the same size; 1.4 sec blanking at med rise after large rise; 1.4 sec blanking at small rise after either med or large rise | 1.4 sec blanking between rises of the same size; 1.4 sec blanking at med rise after large rise; 1.4 sec blanking at small rise after either med or large rise |
| Transmurality indication | Transmurality plateau and after $T_{min}$; $Z_{limit}$ reached; or Any type of rise after $E_{min}$ = 430 J | Transmurality plateau and after $T_{min}$; $Z_{limit}$ reached; or Any type of rise after $E_{min}$ = 380 J | Transmurality plateau and after $T_{min}$; $Z_{limit}$ reached; or Any type of rise after $E_{min}$ = 490 J |
| Others | Ceiling: If TP declared, power level may be Modulated, but may not exceed the power level at the time of TP declaration | N/A | Ceiling: If TP declared, power level may be Modulated, but may not exceed the power level at the time of TP declaration | starting power decreased by one power step (i.e., 15 W). Therefore, a margin can be added so that 420 J can be a minimum energy value.

TABLE 6

Ablation results using fixed 20 W with various time

| Energy (J) | Time (sec) | Partial - Submerged (n = 72) | | Full - Submerged (n = 72) | |
|---|---|---|---|---|---|
| | | Trans (%) | Width (mm) | Trans (%) | Width (mm) |
| 340 | 17 | 31.2 | 2.3 ± 0.9 | 50.0 | 2.3 ± 1.2 |
| 360 | 18 | 56.3 | 2.2 ± 0.7 | 46.4 | 2.4 ± 1.2 |
| 380 | 19 | 100 | 2.3 ± 0.8 | 75.0 | 2.5 ± 1.1 |
| 400 | 20 | 100 | 2.4 ± 1.0 | 100 | 2.5 ± 1.0 |
| 420 | 21 | 100 | 2.4 ± 0.7 | 100 | 2.4 ± 1.2 |
| 440 | 22 | 100 | 2.5 ± 1.1 | 100 | 2.5 ± 1.1 |
| 460 | 23 | 100 | 2.0 ± 0.9 | 100 | 2.9 ± 0.9 |
| 480 | 24 | 100 | 2.9 ± 0.8 | 100 | 3.0 ± 10.7 |
| 500 | 25 | 100 | 2.9 ± 1.1 | 100 | 3.3 ± 0.8 |

Table 7 below illustrates transmurality outcomes for a fixed power value of 10 W to 40 W with 5 W intervals, using different timing to result in 420 J. As shown in Table 7, the powers above 20 W result in 100% transmurality.

TABLE 7

Ablation results of 420 J using various power and time

| Power (W) | Time (sec) | Partial - Submerged (n = 56) | | Full - Submerged (n = 56) | |
|---|---|---|---|---|---|
| | | Trans (%) | Width (mm) | Trans (%) | Width (mm) |
| 10 | 42 | 56.3 | 2.2 ± 1.0 | 46.4 | 2.1 ± 1.1 |
| 15 | 28 | 100 | 2.5 ± 0.8 | 75 | 2.4 ± 0.9 |
| 20 | 21 | 100 | 2.6 ± 0.7 | 100 | 2.5 ± 1.1 |
| 25 | 17 | 100 | 2.5 ± 0.7 | 100 | 2.6 ± 1.1 |
| 30 | 14 | 100 | 2.8 ± 0.9 | 100 | 2.8 ± 1.0 |
| 35 | 12 | 100 | 2.4 ± 1.2 | 100 | 2.9 ± 0.9 |
| 40 | 10.5 | 100 | 2.8 ± 0.8 | 100 | 3.3 ± 1.0 |

In some embodiments, the $E_{min}$ (minimum energy per ablation) value of 450 J can be set by adding 30 J of margin to the presumed minimum energy value (420 J). This minimum energy can be used to set a baseline for the transmural lesion. Therefore, the algorithm can indicate transmurality if there is any sign of impedance profile change (any type of rise detection) after total energy exceeds $E_{min}$.

The method 100 of FIGS. 1 and 2 performs particularly well on fat tissue. Since fat tissue includes little water, it has very high electrical resistivity. Therefore, the fat tissue can prevent RF current flow and can lead to a rapid impedance rise. This can cause termination of ablations due to $Z_{limit}$ or HISO without achieving transmurality. FIG. 14 illustrates test results using the algorithm of FIGS. 1 and 2, showing a high percentage of transmural ablation lesions, even in fat tissue.

The method 100 of FIGS. 1 and 2 can also reduce over-ablation. Compared to the previous algorithms, which maintained the power level at the time of a TP declaration, the method of FIGS. 1 and 2 may actively lower power when there is an impedance rise, for example. If there is excessive sizzling or a temperature rise, especially in thin tissue, the power level can be maintained between 15 W and 20 W, thus lowering the tissue temperature. Table 8 below shows that the rate at which sizzling occurs using the method 100 of FIGS. 1 and 2 to be lower than what would be expected using prior art techniques.

TABLE 8

In vitro testing results using method 100 of FIGS. 1 and 2

| | Time (sec) | Energy (Joules) | HISO (%) | $Z_{limit}$ (%) | Lesion width (mm) | Sizzle (%) | Trans-murality (%) | End at $T_{min}$ (%) |
|---|---|---|---|---|---|---|---|---|
| Bovine (n = 120) | 19.0 ± 0.4 | 483 ± 53 | 0 | 1.7 | 2.6 ± 0.5 | 3.3 | 99.0 | 95.8 |
| Swine (n = 204) | 19.2 ± 1.4 | 447 ± 47 | 0 | 7.4 | 2.6 ± 0.5 | 0.5 | 99.0 | 85.3 |

Figure 15A:
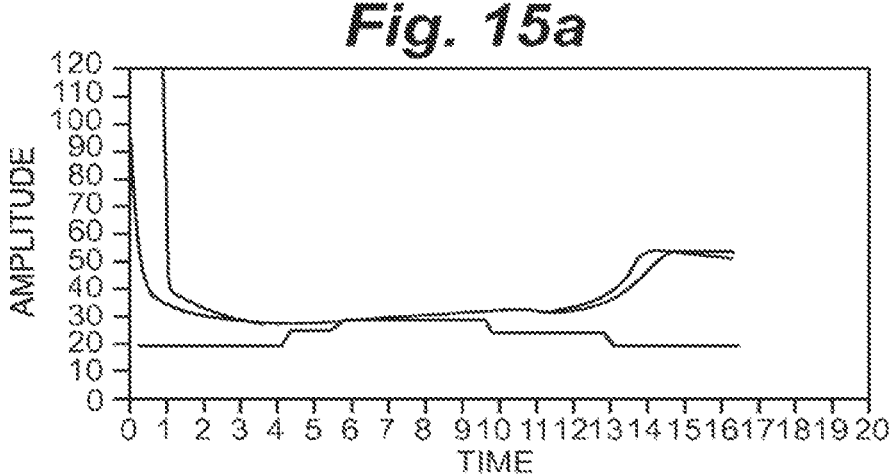
FIG. 15 includes two graphs illustrating the impedance profiles for a one rise step down algorithm according to one embodiment of the invention when rise is detected and either (a) power is decreased by 5 W or (b) power is decreased to zero.
Figure 15B:
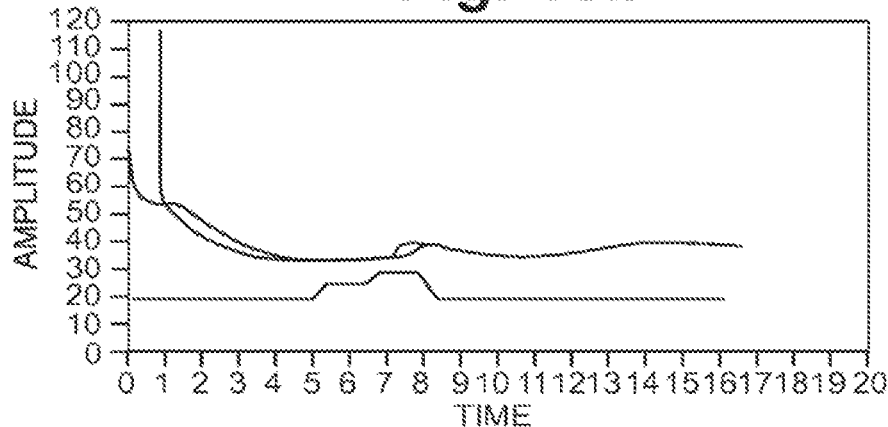

The power modulation algorithm 111 shown in FIG. 2 provides for the identification of three different rise types. However, this number can be increased or decreased. For example, the power modulation algorithm 111 can provide for the identification of one rise type. When a rise is detected, power can be lowered either by a pre-set amount, such as, for example, 5 W, or to the starting power, as shown in FIG. 15, and ablation can continue. The power modulation algorithm 111 can provide for the identification of two rise types, small and large. When a small rise is detected, power can be decreased by a pre-set amount, such as, for example, 5 W. When a large rise is detected, power can be decreased by a pre-set amount, such as, for example, 15 W, or to the starting power. Depending upon the number of rise types identified, various factors, including the maximum time ($t_{max}$) and the minimum time ($T_{min}$), can be adjusted accordingly.

Figure 16:
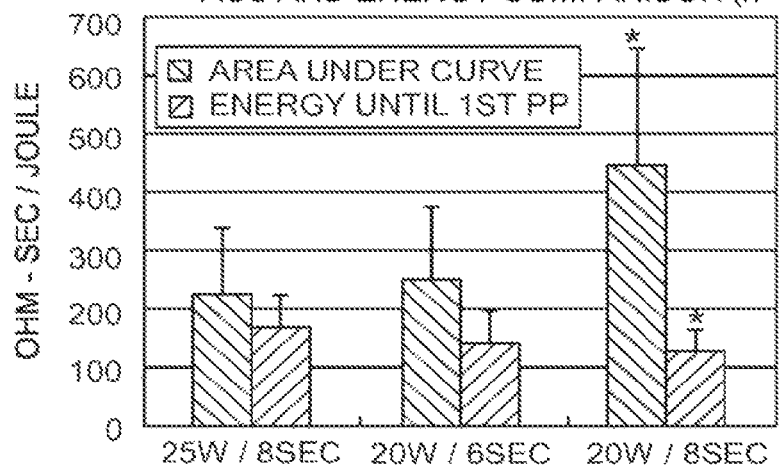
FIG. 16 is a chart illustrating a comparison of Area Under the Curve (AUC) and energy until transmurality plateau detection between different groups of starting power/$t_{max}$.

In FIG. 16, ablation performance until TP detection was compared using a starting power of 20 W, tmax of 6 seconds, and PP criteria (4 out of 5 dZ/dt values>1.3). The area under the impedance curve (AUC) and energy values were compared. AUC can imply impedance decaying characteristics (slope and time), while energy can imply extent of power step up. The 20 W/6 second group shows smaller AUC but greater energy values compared to the 20 W/8 second group. This can indicate relatively faster impedance decaying while applying more power steps compared to 20 W/8 second group, which matches the 25 W/8 second group.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

What is claimed is:

1. A method of applying ablation energy to achieve transmurality at a tissue site, the method comprising:
   applying ablation energy at a first power to the tissue site;
   monitoring impedance of the tissue site;
   reducing the ablation energy applied to the tissue site to a second power in response to a rise in impedance; and
   monitoring total ablation energy delivered, and indicating transmurality if the total ablation energy delivered exceeds a preset minimum following the rise in impedance.

2. The method of claim 1, further comprising applying the ablation energy at an initial power for a start-up blanking period.

3. The method of claim 2, wherein the start-up blanking period is a programmable setting.

4. The method of claim 1, further comprising increasing the ablation energy applied to the tissue site to a third power in response to detecting a power plateau.

5. The method of claim 4, further comprising increasing the ablation energy applied to the tissue site to the third power only if a minimum time at the second power has been met.

6. The method of claim 1, wherein the step of reducing the ablation energy applied to the tissue site includes reducing the ablation energy applied to the tissue site to the second power only if a rise blanking period has expired.

7. The method of claim 1, further comprising:
   terminating delivery of the ablation energy if the total ablation energy delivered exceeds the preset minimum.

8. The method of claim 1, further comprising:
   determining a rate of increase in impedance and assigning the rate of increase in impedance to one of at least three levels following the step of reducing the ablation energy applied to the tissue site.

9. The method of claim 8, wherein the second power is selected based on the one of the at least three levels.

10. The method of claim 1, further comprising:
    indicating transmurality in response to detecting a transmurality plateau following the rise in impedance.

11. The method of claim 10, further comprising:
    terminating delivery of the ablation energy to the tissue site in response to detecting the transmurality plateau following the rise in impedance.

12. The method of claim 1, wherein indicating transmurality is indicated only after the ablation energy has been delivered to the tissue site for a minimum time period following a transmurality plateau.

13. The method of claim 1, wherein the tissue site is an organ wall.

14. The method of claim 1, wherein the tissue site is cardiac tissue.

* * * * *